United States Patent [19]

Bursten et al.

[11] Patent Number: 5,780,237
[45] Date of Patent: Jul. 14, 1998

[54] SEPSIS, ADULT RESPIRATORY DISTRESS SYNDROME, AND SYSTEMIC INFLAMMATORY RESPONSE SYNDROME DIAGNOSTIC

[75] Inventors: Stuart L. Bursten, Snoqualmie; David A. Federighi, Kirkland, both of Wash.

[73] Assignee: Cell Therapeutics, Inc., Seattle, Wash.

[21] Appl. No.: 321,483

[22] Filed: Oct. 12, 1994

[51] Int. Cl.$^6$ .................................................. G01N 33/53
[52] U.S. Cl. ........................... 435/7.1; 436/7.1; 436/161; 436/162
[58] Field of Search .......................... 435/7.32, 7.1; 436/71, 161, 162, 164, 178, 811

[56] References Cited

PUBLICATIONS

Michailov et al., Acta Biologica et medicá Germanica. 32(6):675–680, 1974.
Michailov et al., European Journal of Clinical and Biological Research, 21(10):393–397, 1974.
Akira et al., Proceedings of Congress of the Society of Psychomatic Research on Cardiosvascular Diseases, 25:10–15, 1985.
Quinlan et al., *Free Rad. Res.*, vol. 20, No. 5, pp. 299–306, "Linoleic Acid and Protein Thiol Changes Suggestive of Oxidative Damage in the Plasma of Patients with Adult Respiratory Distress Syndrome", 1994.
Richard et al., *Critical Care Medicine*, vol. 18, No. 1, pp. 4–9, "Vitamin E Deficiency and Lipoperoxidation During Adult Respiratory Distress Syndrome", 1990.

*Primary Examiner*—Paula K. Hutzell
*Assistant Examiner*—Patricia A. Duffy
*Attorney, Agent, or Firm*—Stephen Faciszewski; Cynthia L. Shumate

[57] ABSTRACT

There is disclosed a diagnostic assay for adult respiratory distress syndrome (ARDS), sepsis, multiple organ dysfunction (MOD) and systemic inflammatory response syndrome (SIRS), comprising (a) measuring the amount of selected unsaturated free fatty acids (FFAs) and saturated FFAs in a body fluid, and (b) determining a ratio value comprising the sum of the unsaturated FFAs divided by the sum of the saturated FFAs. There is further disclosed a diagnostic assay for ARDS, sepsis, MOD and SIRS, comprising (a) measuring the amount of 9- or 13-hydroxyoctadecadienoic acid (HODE) and 5-hydroxy-6-trans-8,11,14-cis-eicosatetraenoic acid (5-HETE) in a body fluid, and (b) determining a ratio value of HETE and HODE.

6 Claims, 20 Drawing Sheets

For all (ARDS) samples combined:

```
                    Disease           Total
                    +      -
Test    +    10     2         12
1.45    -           8     15        23
                   18    17         35

Sensitivity   =   10/18 =   0.56
        Specificity   =   15/17 =   0.88
        Accuracy, +   =   10/12 =   0.80
        Accuracy, -   =   15/23 =   0.65
        Likelihood    =   4.67
```

For sepsis (ARDS)

```
                    Disease           Total
                    +      -
Test    +    6      2         8
1.45    -           2     15        17
                    8    17         25

Sensitivity   =   6/8   =   0.75
        Specificity   =   15/17 =   0.88
        Accuracy, +   =   6/8   =   0.75
        Accuracy, -   =   15/17 =   0.88
        Likelihood    =   6.25
```

FIG. 18

SEPSIS, ADULT RESPIRATORY DISTRESS SYNDROME, AND SYSTEMIC INFLAMMATORY RESPONSE SYNDROME DIAGNOSTIC

TECHNICAL FIELD OF THE INVENTION

The present invention provides a diagnostic assay for adult respiratory distress syndrome (ARDS), sepsis, multiple organ dysfunction (MOD) and systemic inflammatory response syndrome (SIRS). The successful method was achieved by examining the proportionality of the distribution of major free fatty acids (FFAs) present in serum of diseased and normal humans and in diseased and normal animal models.

BACKGROUND OF THE INVENTION

ARDS, SIRS, MOD and sepsis are all life-threatening acute diseases that occur in a clinical setting due to trauma or infection and are a result of the body's inflammatory response to fight off the infection or address acute traumatic injury. There are no approved and effective curative treatments and the diseases are treated with medical intervention of the symptoms or ultimate causative agents (e.g., respirators, fluids, antibiotics, β-agonists, surgery, etc.). Moreover, there are no early diagnostic tests for the diseases and only presence of symptoms (e.g., respiratory distress, hypotension, fever/chills) have been used to diagnose, ARDS, SIRS and sepsis is susceptible patients. Each of the diseases is acutely life-threatening and leads to multiple organ dysfunction (MOD) and permanent disabilities for the survivors.

Despite the tremendous advances in resuscitation of trauma victims in the last ten years, large numbers of these victims subsequently die of multiple organ dysfunction (MOD) with or without associated sepsis. In order to prevent such deaths, therapeutic regimens concentrating on modulation of the complex pathophysiology of trauma and ensuing MOD must be investigated.

In the United States physical injury remains the leading cause of death during the first three decades of life (Trunkey, *Sci. Amer.* 249: 28–35, 1983). Fifty to 75% of trauma deaths occur in a group of people ranging from 15 to 44 years of age. There are more years of productive life lost from traumatic injuries than from AIDS, heart disease and cancer combined. Such injuries account for over 100,000 deaths each year and rank overall as the fourth leading cause of mortality in the US. Approximately 75% of the deaths following trauma occur from exsanguination, catastrophic internal, or central nervous system injury either immediately or within the first one to two hours after injury. The other 25% of deaths occur in patients who survive the first one to two hours after injury and are admitted to the hospital alive. The vast majority of these trauma victims die due to MOD (Trunkey, *Sci. Amer.* 249:28–35, 1983). Deaths from injury which occur either immediately or within the first hour of injury can only be prevented by preventing the accident itself. However, the vast majority of deaths that occur once a patient is hospitalized could be prevented by therapeutic regimens which prevent and/or reverse MOD.

Trauma and hemorrhagic shock are two of the major known risk factors for developing Adult Respiratory Distress Syndrome (ARDS) and MOD. Even though the mechanism of MOD remains to be elucidated, it is generally accepted that a combination of four potential mechanisms is involved including: i) ischemia reperfusion injury mediated by reactive oxygen species; ii) over activity of the cellular and molecular mediators of the inflammatory response (interleukin-1 (IL-1), tumor necrosis factor (TNF), platelet activating factor (PAF), complement, eicosanoids, nitric oxide, etc.), iii) leukocyte-endothelial cell interactions, and iv) maldistribution of blood flow causing additional tissue hypoxia. The common elements in each of these four potential interrelated mechanisms are hypoxia and oxidative injury leading to over production of inflammatory cytokines and leukocyte-endothelial cell interaction (Cipoll et al., *Crit. Care Clin.* 9:261–298, 1993). It is likely that the initial insult leading to these phenomena is tissue hypoxia. Studies in animals and humans provide evidence of increased levels of inflammatory cytokines including TNFα, IL-1α and β, and related secondary inflammatory mediators such as IL-6, IL-8, and PAF that participate in a cytokine cascade that directly or indirectly cause organ dysfunction by activating endothelium and neutrophils. In fact, the complex cascade of mediators released following resuscitation after severe blood loss appears to progress in a similar fashion to those observed following sepsis and septic shock, despite the fact that hypoxia rather than bacterial endotoxin or other bacterial products is the major initiator of these events following hemorrhage. In experimental animals, TNFα appears to be the first cytokine produced followed by IL-6, prostaglandin $E_2$ ($PGE_2$), and transforming growth factor beta (TGF-β) at later time points following the initiation of hemorrhagic shock (Vedder et al., *J. Clin. Invest.* 81:939–944, 1988). In these models, organ injury and mortality could be significantly reduced by blocking neutrophil adhesion with a monoclonal antibody directed against the primary human neutrophil adherence glycoprotein, CD-18. Unfortunately, subsequent studies have demonstrated that this monoclonal antibody to CD-18 also increases the susceptibility to bacterial infection in a rabbit model (Sharar et al., *Surgery* 110:213–220, 1991).

The pathophysiology of MOD after trauma is also complicated by the fact that there may be at least three major scenarios by which it occurs. The first scenario is a massive overwhelming inflammatory response from the initial injury, shock, and resuscitation which leads to MOD in the ensuing two to three days (Faist et al., *J. Trauma* 23:775–787, 1983). A second scenario involves a more delayed onset of MOD because the initial insult was not sufficient to cause overwhelming MOD, but is sufficient to prime the inflammatory cells such that subsequent stimuli like an infection or additional operative intervention may lead to an overwhelming inflammatory response and organ failure which may occur as long as a week or two after injury (Gorris et al., *Arch. Surg.* 120:1109–1115, 1985). In the third scenario, the initial injury and derangement of the immunologic and inflammatory response make the patient more susceptible to bacterial infection leading to sepsis which then leads to MOD (Faist et al., *J. Trauma* 23:775–787, 1983). The common element in each of these three scenarios is an early activation of the systemic inflammatory response which varies only in degree.

The current therapy for severely injured patients with hemorrhagic shock is control of bleeding, debridement of devitalized tissue, fracture fixation, rapid and effective resuscitation with eradication of sub-clinical flow-dependent oxygen consumption and metabolic support with enteral and parenteral nutrition. Despite these basically supportive advances in the treatment of severely injured patients, only modest reductions in ARDS, MOD and mortality have been realized. It is clear that further advances will require therapy targeted at the inflammatory mediators responsible for the severe over activity of the systemic inflammatory response which appear to be the final common pathway to organ injury.

The central theme in treating MOD caused by any one of ARDS, SIRS, trauma and sepsis is that the earliest diagnosis, preferably prior to symptom onset can help treat MOD. There is a need in the art to provide such a diagnostic tool, rather than an assessment of symptoms and symptom severity that currently exist. The present invention was made to provide such a diagnostic tool that can quantitatively and qualitatively assess MOD, ARDS, SIRS and sepsis by a simple test.

SUMMARY OF THE INVENTION

The present invention provides a diagnostic assay for adult respiratory distress syndrome (ARDS), sepsis, multiple organ dysfunction (MOD) and systemic inflammatory response syndrome (SIRS), comprising (a) measuring the amount of selected unsaturated free fatty acids (FFAs) and saturated FFAs in a body fluid, and (b) determining a ratio value comprising the sum of the unsaturated FFAs divided by the sum of the saturated FFAs. Preferably, the unsaturated FFAs are at least one selected from the group consisting of linoleate, oleate, arachidonate, and combinations thereof. Preferably, the saturated FFAs are at least one selected from the group consisting of myristate, palmitate, stearate, and combinations thereof. Preferably, the ratio value comprises the sum of linoleate plus oleate, divided by palmitate.

Preferably, the body fluid is plasma or a plasma-sourced body fluid (e.g., urine, sweat, saliva or tears). There are several means for measuring the amount of selected FFAs. These include, for example, HPLC (high performance liquid chromatography), GC (gas chromatography), TLC (thin layer chromatography), and immunoassays using antibodies specific for the specific FFAs.

Alternatively, the present invention provides a diagnostic assay for adult respiratory distress syndrome (ARDS), sepsis, multiple organ dysfunction (MOD) and systemic inflammatory response syndrome (SIRS), comprising (a) measuring the amount of 9- or 13-hydroxyoctadecadienoic acid (HODE) and 5-hydroxy-6-trans-8,11,14-cis-eicosatetraenoic acid (5-HETE) in a body fluid, and (b) determining a ratio value of HETE and HODE.

BRIEF DESCRIPTION OF THE DRAWINGS

FIG. 18 shows the Bayesian analysis for the ration at 24 hr using a 1.45 ratio descriminator.

DETAILED DESCRIPTION OF THE INVENTION

Figure 1:
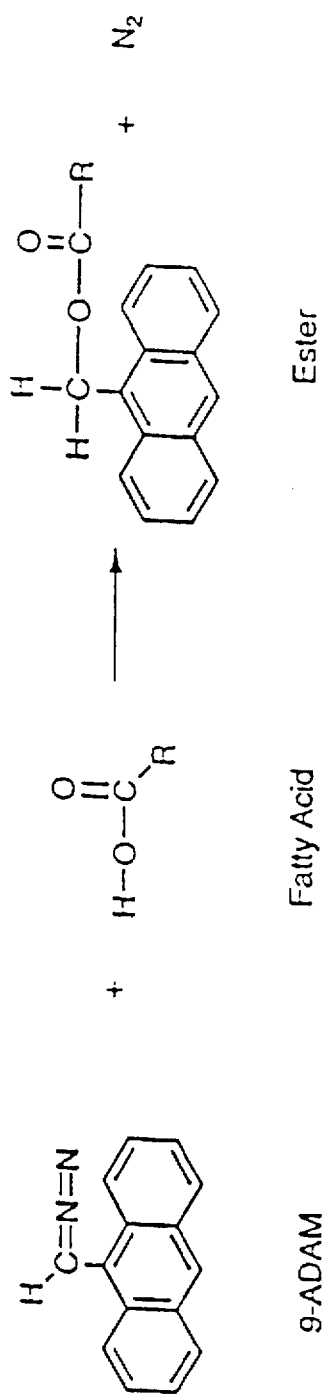
FIG. 1 illustrates the chemistry of a reaction to derivatize FFAs with 9-ADAM.

The present invention provides a diagnostic assay for adult respiratory distress syndrome (ARDS), sepsis, multiple organ dysfunction (MOD) and systemic inflammatory response syndrome (SIRS), comprising (a) measuring the amount of selected unsaturated free fatty acids (FFAs) and saturated FFAs in a body fluid, and (b) determining a ratio value comprising the sum of the unsaturated FFAs divided by the sum of the saturated FFAs. Preferably, the unsaturated FFAs are at least one FFA selected from the group consisting of linoleate, oleate, arachidonate, and combinations thereof. Preferably, the saturated FFAs are selected from the group consisting of myristate, palmitate, stearate, and combinations thereof. Preferably, the ratio value comprises the sum of linoleate plus oleate, divided by palmitate.

We developed the notion that FFAs play a role in MOD through a study of various phospholipids in disease processes and by developing therapeutic agents for such diseases acting on the disease process and not by addressing the symptoms. We eventually developed a method to predict the onset of ARDS and MOD by examining the proportionality of the major free fatty acids present in serum. We analyzed FFAs in serum and studied which FFAs could be measured using a reverse phase HPLC technique. The ratio of the sum of linoleate plus oleate, divided by palmitate, we were able to predict ARDS and MOD as later manifestations of sepsis, SIRS and traumatic injury problems. This diagnostic assays allows for early detection of ARDS and MOD to allow for treatment and actual prevention of ARDS and MOD in septic and trauma patients at risk. The use of the term "trauma" encompasses a wide range of traumatic injury, including, for example, burns, smoke inhalation, toxic epidermal drug reactions, active trauma, and combinations thereof.

Generally a ratio of one or a sum of several unsaturated FFAs (in the range of C14 to C22) divided by one or a sum of several saturated FFAs (in the range of $C_{14}$ to $C_{22}$) correlated with ARDS and MOD in frozen human serum samples and in animal models. Since unsaturated FFAs are measured, it is important to prevent oxidation of the sample by immediately freezing at low temperatures and by storing in an inert atmosphere (e.g., argon or nitrogen).

Preferably, a ratio is (linoleate+oleate)/palmitate due to several reasons. First, levels of HETE or HODE were below detectable limits of assay systems attempted. Either HETE and HODE do not accumulate appreciably in lung tissue in a rat model used or these chemically and metabolically labile compounds degraded before analysis during shipment and storage. Second, linoleate activates $PLA_2$ in the inflammatory response and its circulating levels should increase. Third, $PLA_2$ hydrolyzes the sn-2 acyl chains of phospholipids. Unsaturated acyl chains are found in the sn-2 position of phospholipids, while saturated chains are at the sn-1 position. Such changes were observed in the oleate levels. Finally, palmitate is a major constituent of the serum FFA pool. It is found in the sn-1 position of phospholipids. As such it should not increase with $PLA_2$ activation, and dividing by palmitate allows the ratio indicator to be independent of protein measurement. These experimental results are preferable to examination of minimally detectable HETEs and HODEs.

The choice of a means for measuring FFAs can be any means to measure and distinguish FAs in the $C_{14}$–$C_{22}$ range and distinguish saturated from unsaturated FFAs. Preferred means include TLC (thin layer chromatography), reverse phase HPLC, GC and immunoassays. It is also referable to first conjugate the FFAs to a conjugation molecule to better detect and distinguish FFAs.

A normal "oxidative burst" in phagocytizing cells in response to bacterial, fungal, or viral insult is caused by generating reactive oxygen species including hydrogen peroxide ($H_2O_2$), hydroxide radical (OH.) and superoxide anion ($O.^{2-}$). Cells also must provide protection from overproduction of chemically reactive species. This is accomplished by glutathione and ubiqinonol, and the enzymes glutathione peroxidase, superoxide dismutase, and catalase. Within a biological membrane, vitamin E ($\alpha$-tocopherol), acts as an antioxidant to minimize or prevent lipid peroxidation.

Lipid peroxidation occurs within unsaturated (2 or more double bonds) acyl side chains of phospholipids by abstraction of a hydrogen atom. Lipid peroxidation is initiated by a reactive radical such as the superoxide anion and is self propagating because the products are peroxy- and hydroperoxy lipids (containing a new free radical that can initiate another cycle of reactions). Lipid peroxidation reactions are catalyzed by inorganic ions such as iron and copper.

Lipid hydroperoxidations can be produced by the actions of endogenous cyclooxygenase and lipooxygenase enzymes. Lipooxygenases and cyclooxygenases produce prostanoids and leukotrienes from either arachidonic acid (20:4) or eicosapentenoic acid (20:5). These enzymes can also use linoleic acid (18:2) as a substitute to produce HODE as well as hydroxylated products of arachidonic acid, such as 5-HETE. The dihydroxylated product of this reaction is leukotriene $B_4$.

Vascular endothelial cells produce an endogenous level of the metabolites of both arachidonic acid and linoleic acid. In these cells, HODE is synthesized through a monohydroperoxyl intermediate to form hydroxyl derivatives (Funk et al., *J. Biol. Chem.* 260:7481–7488, 1985). Moreover, 13-HODE accumulates in artherosclerotic aortas of human and hyperlipidemic rabbits (Mowri et al., *Biochem. Int.* 12:347–352, 1973). The level of arachidonic acid is increased by the hydrolysis of the C-2 acyl chain of endogenous phospholipids, mainly phosphatidyl inositol and phosphatidyl choline, by the action of Phospholipase $A_2$ ($PLA_2$).

Lipopolysaccharides (LPS), an endotoxin responsible for initiating a sepsis inflammatory cascade, stimulates lipooxygenase to synthesize 13-HODE (Schrade et al., *Biochem. Biophys. Res. Comm.* 147:695–700, 1987). 13-HODE can inhibit thromboxane $A_2$ synthesis and increase the production of prostacyclin in endothelial cells and 12-HETE from platelets (Setty et al., *Biochem. Biophys. Res. Comm.* 148:528–532, 1987). When human platelets were stimulated with the pathogen *Toxoplasma gondii*, they released thromboxane $B_2$, 9-HODE, and 13-HODE into the circulation (Henderson Jr. et al., *Biochemistry* 31:5356–5362, 1992).

Phospholipase D (PLD) hydrolyzes choline and ethanolamine head groups from endogenous phospholipids to produce phosphatidic acid (PA). $H_2O_2$ causes activation of PLD in endothelial cells. The peroxide derivative of linoleic acid, C18:2-OOH, can also activate PLD (Natarajan et al., *J. Biol Chem.* 268:930–937, 1993). The PA that is produced by PLD can stimulate lyso-PA acyltransferase (LPAAT) to produce additional PA.

In the early stages of a septic state, LPS stimulates the production of oxygen reactive radicals which initiate lipid peroxidation and the enzymes required to produce both precursors and HODEs and HETEs. The increase in circulating levels of HODEs and HETEs add to a negative cascade of events that can lead to septic shock, ARDS, SIRS and MOD. This process has been implicated in a large group of pathological conditions including: glomerulonephritis, vasculitis, autoimmune diseases, rheumatoid arthritis, radiation injury, emphysema, hyperoxia, bronchopulmonary dysplasia, and endotoxic liver injury (Halliwell, *FASEB J.* 1:358–364, 1987). Therefore, the inventive method has a potential for wide applications as a diagnostic tool due to its focus upon a common mechanism of disease action, including each of the foregoing diseases.

The present invention is based upon the foregoing foundation that changes in serum levels of FFAs are indicators of the onset of a large number of diseases that lead to MOD, including, but not limited to sepsis, ARDS, and SIRS. In a preferred embodiment, it is necessary to quantitatively separate these specific FFAs from the other lipids found in serum by a combination of chemical extraction of FFAs from the biological fluid and chromatography to separate and detect FFAs in the $C_{14}$–$C_{22}$ range and distinguish saturated from unsaturated FFAs. Chemical extraction can be accomplished, for example, by the method of Bligh et al. (*Canadian J. Biochem. Physiol.* 37:914–917, 1959) or that of Folch et al. (*J. Biochem.* 226:497–509, 1957). Briefly, the method of Bligh et al. involves an organic extraction of lipids from biological tissue homogenates or fluids. One volume of sample and three volumes of methanol:chloroform (2:1) are vigorously shaken for 2 min. One volume of chloroform is added and then shaken vigorously for 30 sec. One volume of water is added and then shaken vigorously for 30 sec. The mixture is filtered and the upper aqueous layer is discarded. The lower organic layer contains a mixture of lipid classes, including FFAs. The method of Folch et al. involves the extraction of lipids from biological tissue homogenates or body fluids. One volume of sample plus 20 volumes of chloroform:methanol (2:1) are vigorously shaken for 2 min. The mixture is filtered and an amount of 0.1N KCl equal to 20% of the extraction mixture volume is added and the mixture is shaken vigorously for 2 min. The aqueous and organic phases are allowed to separate. The upper aqueous layer is discarded. The lower organic layer contains a mixture of lipid classes, including FFAs. Free fatty acids and neutral lipids can be separated from phospholipids by normal phase high performance liquid chromatography (HPLC) by modifying the method of Van Kessel et al. (*Biochim et Biophys Acta* 486:524–530, 1977). This method involves separation of lipids into their major classes by normal phase (silica) high performance liquid chromatography (HPLC). A 5 micron, 25 cm×0.45 cm silica HPLC column is connected to a binary solvent delivery system followed with a UV detector. The lipid sample is injected on the column and a solvent gradient is run at 1.0 ml/min. The solvent gradient is hexane:isopropanol:water in the proportions 3:4:0.75 run isocratically for 3 min, then ramped to hexane:isopropanol:water in the proportions 3:4:1.4 in 15 min, then run isocratically at the same proportions for 15 min. Detection is at 206 nm. The FFAs and neutral lipids elute in the first 5 min.

Gas-liquid chromatography (GLC) with flame ionization or mass detection is a preferred method for FFA analysis (Christie, *High-performance Liquid Chromatography and Lipids*, Pergamon Press 1987). This method uses open fused silica columns to separate derivatized FFAs at a relatively low cost with high sensitivity and good quantitation, but the high injection temperatures (e.g., 190° C.) involved risks thermal degradation of the unsaturated FFAs before detection. Methods using reverse phase HPLC with Ultraviolet (UV) or fluorescent detection are most preferred. Published methods have coelution problems especially with oleic acid (C18:1) and palmitic acid (C16:0). We have developed a preferred HPLC method to separate and quantitate the FFAs of interest. The preferred method is described in examples 1 and 2.

EXAMPLE 1

This example illustrates a preparation of anthroyl fatty acid derivatives. Fatty acid derivatives of 9-anthroyl diazomethane (9-ADAM), which absorbs light at 254 nm and fluoresces with emission at 410 nm, were prepared essentially according to the method described in Nakaya et al.(*Bull. Chem. Soc. Japan* 40:691–692, 1967, and Yoshida et al., *Analytical Biochem.* 173:70–74, 1988). The derivatization is based on the reaction shown in FIG. 1. Briefly, 9-anthraldehyde hydrazone for 9-anthroyl diazomethane derivatization was synthesized from 9-anthraldehyde and hydrazine monohydrate as follows: (a) 8.8 g 9-anthraldehyde (Aldrich Milwaukee, Wis.) was dissolved in 150 mL absolute ethanol and 8 mL hydrazine monohydrate (Aldrich Milwaukee, Wis.) was added dropwise with continual stirring. (b) The mixture cleared as hydrazine was added then turned opaque as the last drops were added. (c) The reaction was stirred at room temperature for 3 hr, then was filtered (Whatman #1 filter paper, Whatman Int. Maidstone UK) and dried. (d) The product was recrystalized twice with absolute ethanol. (e) The yield was 3.1 g of needle-like crystals.

Figure 2:
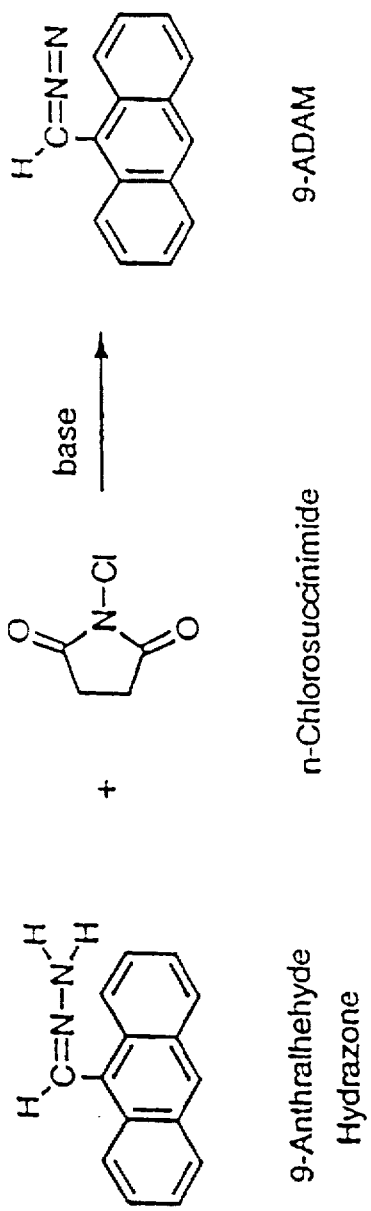
FIG. 2 illustrates the chemistry of a reaction to make a 9-ADAM derivatizing reagent.

The following solutions were made in ethyl acetate: 9-anthraldehyde hydrazone (0.0276M, 0.0304 g/5 mL), Quinuclidine (0.2760M, 0.1534 g/5 mL (oxidizing reagent)), and N-chlorosuccinimide (0.0276M, 0.0184 g/5 mL (catalyst)). Equal volumes of these solutions were mixed to react at room temperature for 30 min. The resulting 9-anthryl diazomethane (9-ADAM) was unstable and was made fresh daily. This reaction is shown in FIG. 2.

The derivatizating reaction was carried out by diluting 50 µL of each FFA standard to 200 µL with methanol. FFA standards (1.0 mg/mL) were made up in methanol using: Heptadecanoic acid 17:0 (Aldrich Chemical Milwaukee, Wis.); Arachidonic acid 20:4 (Matreya, Inc., Pleasant Gap, Pa.); Linoleic acid 18:2 (Matreya, Inc., Pleasant Gap, Pa.); Linolenic acid 18:3 (Matreya, Inc., Pleasant Gap, Pa.); Palmitic acid 16:0 (Matreya, Inc., Pleasant Gap, Pa.); Oleic acid 18:1 (Matreya, Inc., Pleasant Gap, Pa.); Stearic acid 18:0 (Matreya, Inc., Pleasant Gap, Pa.); Myristic acid 14:0 (Matreya, Inc., Pleasant Gap, Pa.); Lauric acid 12:0 (Matreya, Inc., Pleasant Gap, Pa.); Arachidic acid 20:0 (Matreya, Inc., Pleasant Gap, Pa.); and n-Docosanoic acid 22:0 (Matreya, Inc., Pleasant Gap, Pa.). Additionally, the following standards were dissolved in methanol (50 µg/mL): 5-HETE 20:4; 12-HETE 20:4; and 13-HODE 18:2 (Biomol Research Laboratories, Inc., Plymouth Meeting, Pa.). Derivatizing solution (200 µL) was added. The mixture was reacted for 1 hr at room temperature to form each derivatized standard. 20 µL was injected into an HPLC and run by a reverse phase method described below.

EXAMPLE 2

This example illustrates the reverse phase HPLC procedure used to separate and quantitate the derivatized anthroyl FFAs. A reverse phase "C8" column (4.6 cm×25 cm, 5 micron Spherisorb® C8, Alltech Associates, Inc. Deerfield, Ill.) separated the saturated FFAs, and a reverse phase "C18" column (4.6 mm×15 cm, 3 micron Spherisorb® ODS2 Alltech Associates, Inc. Deerfield, Ill.) separated the unsaturated FFAs. Neither column individually could resolve all the derivatized FFA standards. To solve the problem, a 3 micron, 15 cm "C18" column was connected to the HPLC followed by a 5 micron, 25 cm "C8" column. The high performance liquid chromatograph was a model 517 from Gilson Medical Electronics, Inc., Middleton, Wis. Two detectors were connected in tandem. The first was Model UVIS 200 from Linear Instruments, Reno, Nev.. The second was Model 121 Fluorometer from Gilson Medical Electronics.

Table 1 below shows the chromatographic conditions used.

TABLE 1

| | |
|---|---|
| UV Detection: | 254 nm |
| Fluorescent Detection: | Excitation: 305–395 nm bandpass filter |
| | Emission: 430–470 nm bandpass filter |
| Buffer A: | 70% Acetonitrile: 30% $H_2O$ |
| Buffer B: | 100% Acetonitrile |
| Flow: | 1.0 mL per min |
| Gradient: | 40% B for 2 min |
| | from 40% to 45% B in 18 min |
| | from 45% to 54% B in 10 min |
| | from 54% to 70% B in 5 min |
| | from 70% to 94% B in 19 min |
| | from 94% to 99% B in 1 min |

TABLE 1-continued

```
99% B for 29 min
from 99% to 40% B in 1 min
40% B for 5 min
```

Figure 3:
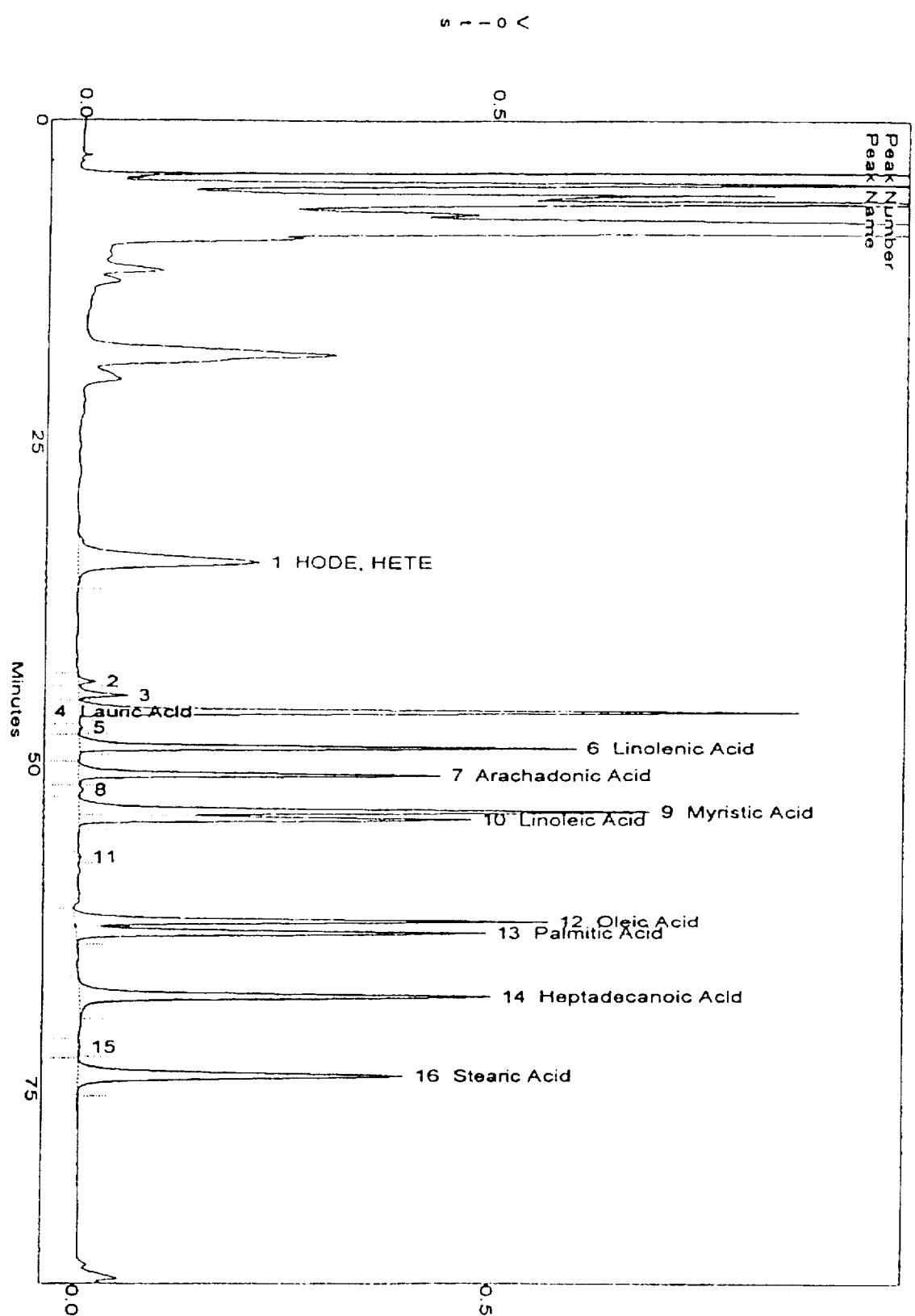
FIG. 3 shows a chromatogram of 9-ADAM derivatized FFA standards using the HPLC reverse phase method described in example 2 using UV detection at 254 nm.
Figure 4:
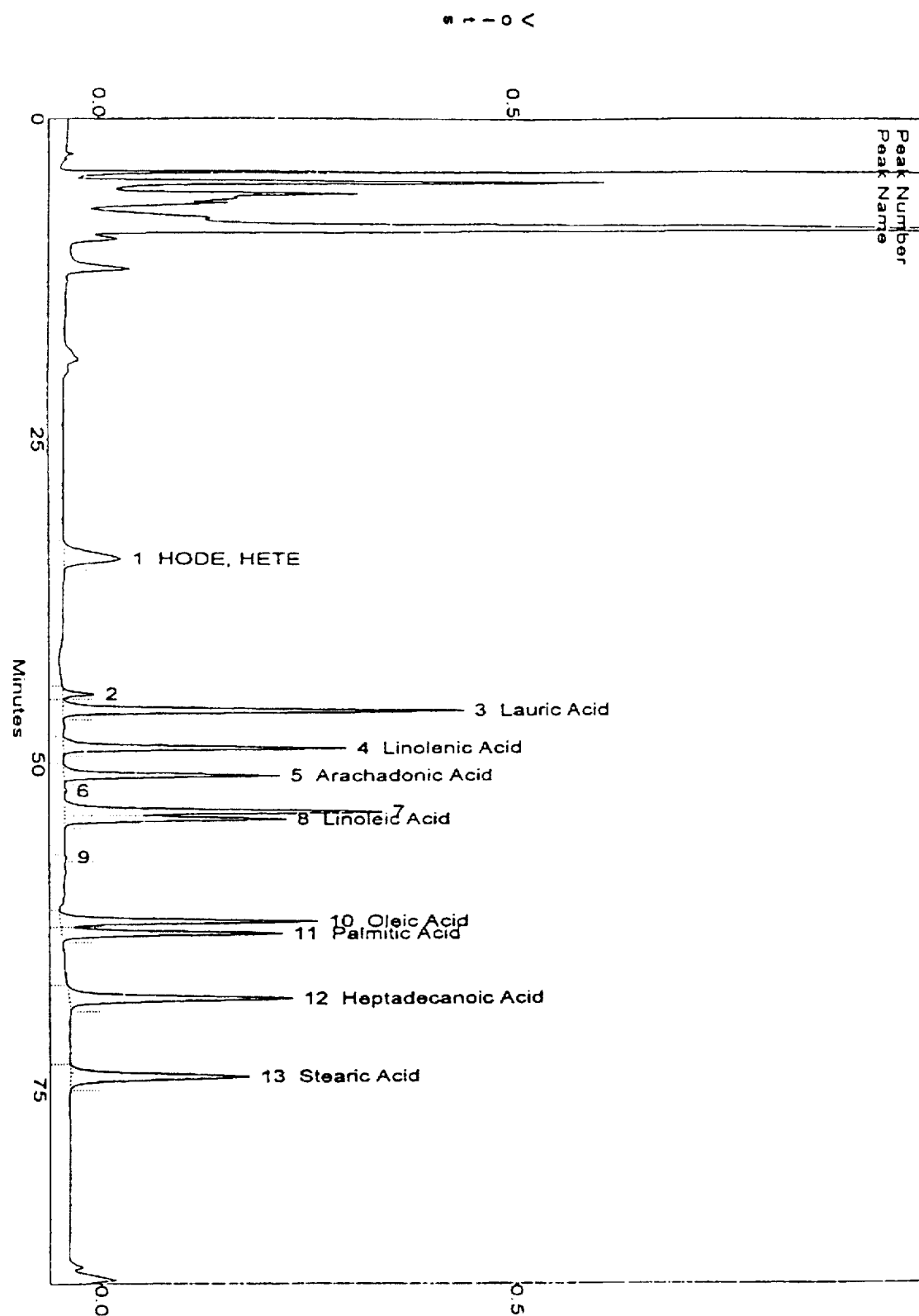
FIG. 4 shows a chromatogram of 9-ADAM derivatized FFA standards using the HPLC reverse phase method described in example 2 using fluorescence detection.

Using the HPLC system described, we separated individual derivatized FFAs. FIG. 3 shows a chromatogram of standards detected by ultraviolet (254 nm) absorption while the same sample detected by fluorometric emission (ex 350 nm, em 410 nm) is shown in FIG. 4. Levels of detection were in low nanogram quantities. Once separation and quantitation of FFA levels was achieved an animal model was examined in example 3.

EXAMPLE 3

This example illustrates an animal model of sepsis and ARDS wherein a diagnostic assay analyzing derivatized anthroyl FFAs from rat lungs was done. Frozen perfused rat lungs were received from the Webb-Waring Institute (University of Colorado) and stored at −70° C. until analyzed in a blinded manner wherein the operator was unaware of the condition of the animal from each lung source.

The analysis procedure was: (1) 25 µL of heptadecanoic acid was added to a 10 mL conical ground glass homogenizing tube and dried under a stream of nitrogen at 35° C. for use as an internal standard. (2) A pair of perfused rat lungs and 1.0 mL distilled water were added and the tissue was ground by hand at 4° C. with a ground glass pestle. (3) 1.0 mL homogenate was extracted by the method of Folch et al. (infra.). Briefly, 1 ml of homogenate was analyzed. The sample, plus a volume of chloroformn:methanol (2:1) 20 times the sample volume, were shaken vigorously for 2 min. The sample was vacuum filtered through GF/F sintered glass filters (Whatman Int. Maidstone UK). A volume of 0.1N KCl equal to 20% of the filtrate was added and the sample was vigorously shaken. The sample was spun at 1200 rpm for 7 min to break the emulsion and allow phase separation. The upper aqueous phase was discarded. The lower organic phase contained the extracted lipid classes and was saved for analysis. The rest of the sample was stored at −20° C. until all samples were extracted at which time a protein determination was made by the Pierce BCA method. (4) The chloroform:methanol phase was dried under a stream of nitrogen at 35° C. (5) The samples were redissolved in 200 µL hexane:isopropanol (3:4), vortexed for 5 min, sonicated for 5 min, and transferred to glass HPLC injection vials. (6) 190 µL of sample were run on the HPLC according to the method described in example 2 and the eluent was collected for the first 5 min post-solvent front. This fraction contained the FFAs and was dried under a stream of nitrogen at 35° C. (7) 200 µL of methanol were added to each sample and the sample was derivatized as in example 1. (8) 20 µL of sample were run by the reverse phase HPLC method described in example 2. (9) Combined FFA standards of 1250 ng, 625 ng, 312 ng, 156 ng, and 78 ng were derivatized and run as above to create a standard curve. (10) The unknowns were quantified, corrected for extraction efficiency, and calculated per mL serum.

Figure 5:
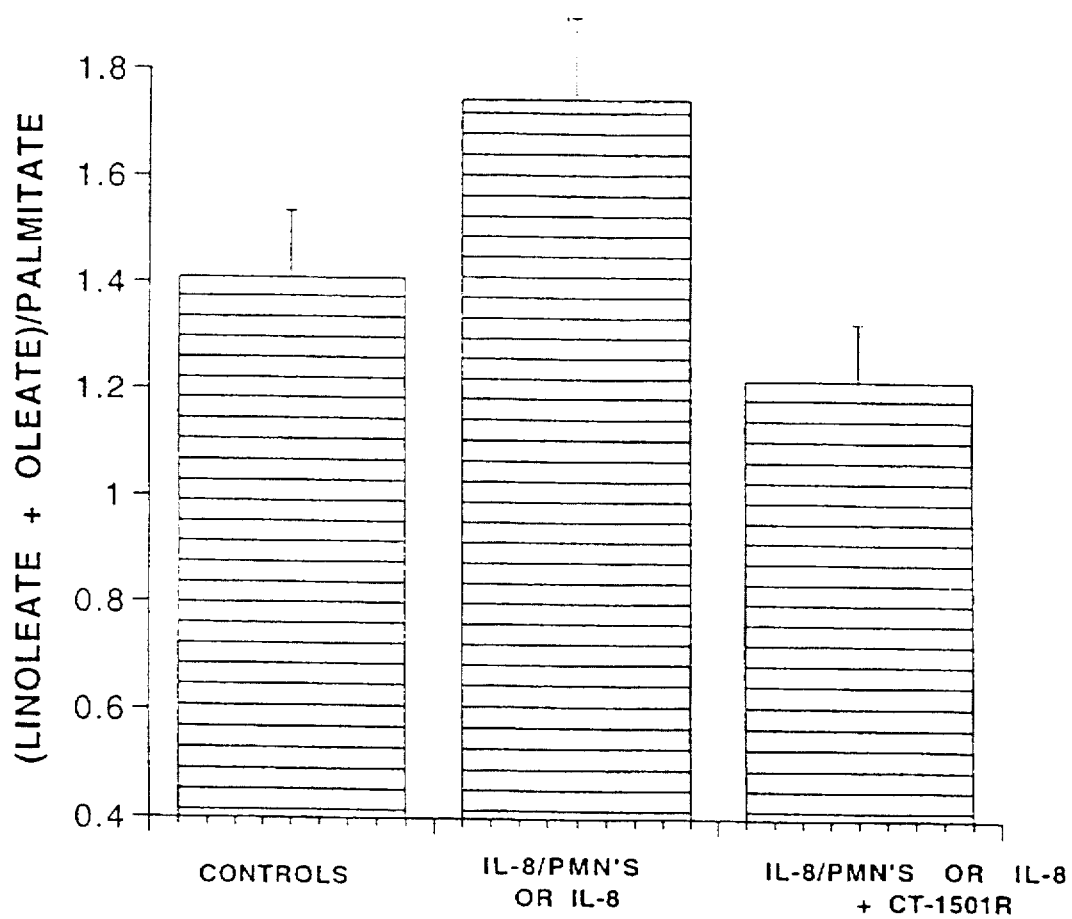
FIG. 5 shows the effect of inflammation on the ratio of (linoleate+oleate) divided by palmitate in rat lungs. Septic animals show a significantly higher FFA ratio than control animals. This effect was moderated by lisofylline.

The perfused lungs of three groups of rats were received from the Webb-Waring Institute (University of Colorado) Denver Colo.: Group I consisted of normal animals; Group II animals were treated with IL-8 and/or polymorphonuclear cells (PMN's) to mimic ARDS; and Group III animals were treated with IL-8 and lisofylline (a substituted xanthine therapeutic agent that is under clinical investigation for treatment of sepsis, SIRS, ARDS (trauma) and other diseases manifest as MOD). FIG. 5 shows changes in the means of the ratio of (linoleate+oleate)/palmitate. The "septic" Group II showed a significantly higher linoleate plus oleate divided by palmitate ratio than the Group I controls. This level was reduced by lisofylline in Group III. These data show a strong correlation for the preferred ratio and development of clinical symptoms of MOD and ARDS. These data further show that lisofylline is an effective agent for treatment or prevention of the foregoing diseases and conditions.

EXAMPLE 4

This example illustrates an analysis of derivatized anthroyl FFAs in human serum. Frozen human serum samples were received from the Webb-Waring Institute and stored at −70° C. until analyzed. The Webb-Waring Institute provided two sets of serum samples from patients admitted to their trauma center. All patients had medium to high APACHE scores, and many had underlying diseases. The first set of samples were time courses drawn at the time of admission then 6 hr, 12 hr, 24 hr, and 48 hr post admission. The second set included the same time courses, but also single samples of patients drawn 24 hr post-admission. In addition, the serum of healthy individuals employed at CTI (Seattle, Wash.) were also analyzed.

The samples were analyzed in a blinded manner as follows: (1) 25 µL of heptadecanoic acid standard was added to a 15 mL conical glass centrifuge tube and dried under a stream of nitrogen at 35° C. (2) 0.5 mL human serum was added to the tube and extracted by the method of Folch et al. (infra.) as described above in example 3. (3) The chloroform:methanol phase was dried under a stream of nitrogen at 35°C. (4) The samples were re dissolved in 200 µL hexane:isopropanol (3:4), vortexed for 5 min, sonicated for 5 min, and transferred to glass HPLC injection vials. (5) 190 µL of sample were run on the HPLC as described above in example 2, and the eluent was collected for the first 5 min post solvent front. This fraction contained the FFAs and was dried under a stream of nitrogen at 35° C. (6) 200 µL acetone were added to each sample and the sample was derivatized as above. (8) 20 µL of sample was run by the reverse phase method described in example 2 above. (9) Combined FFA standards of 1250 ng, 625 ng, 312 ng, 156 ng, and 78 ng were derivatized and run as above to create a standard curve. (10) The unknowns were quantified, corrected for extraction efficiency, and calculated per mL serum.

Figure 6:
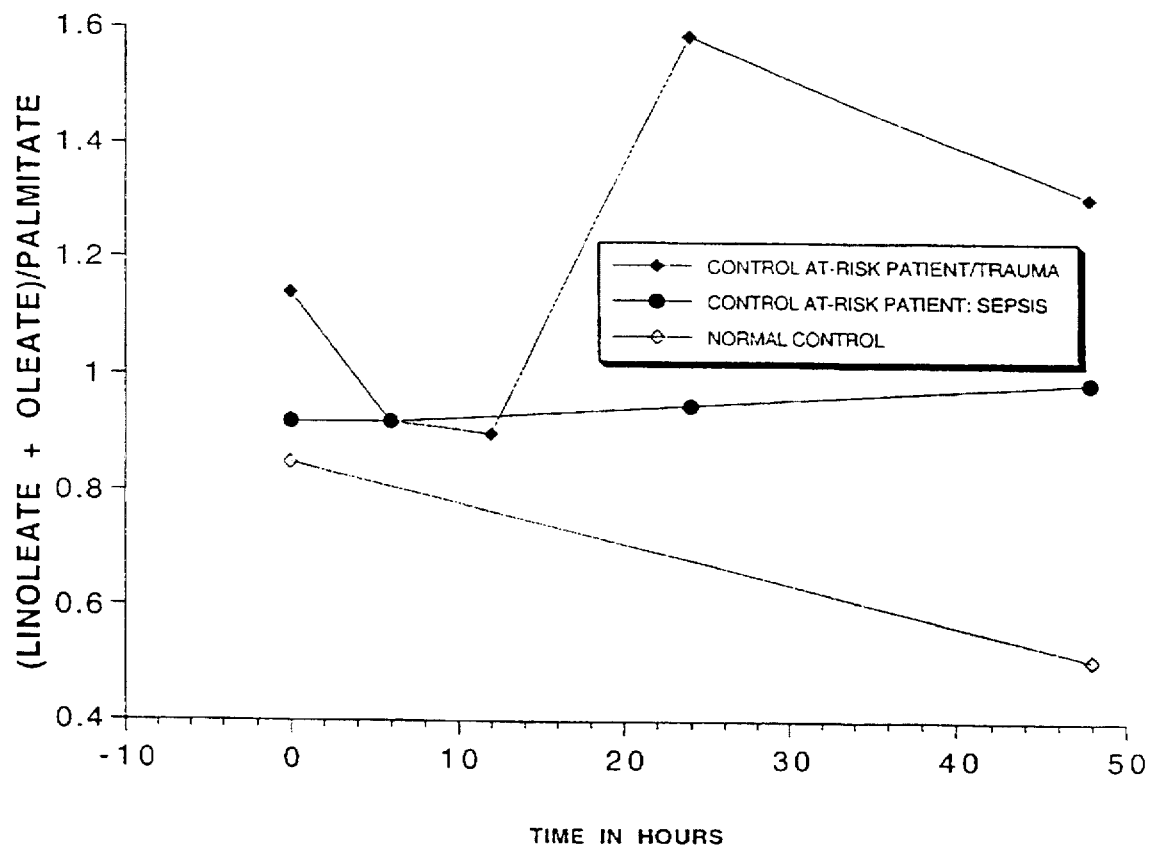
FIG. 6 shows the ratio of (lioleate+oleate) divided by palmitate in control patients admitted to a trauma center. The patients were at risk, but did not develop ARDS.
Figure 7:
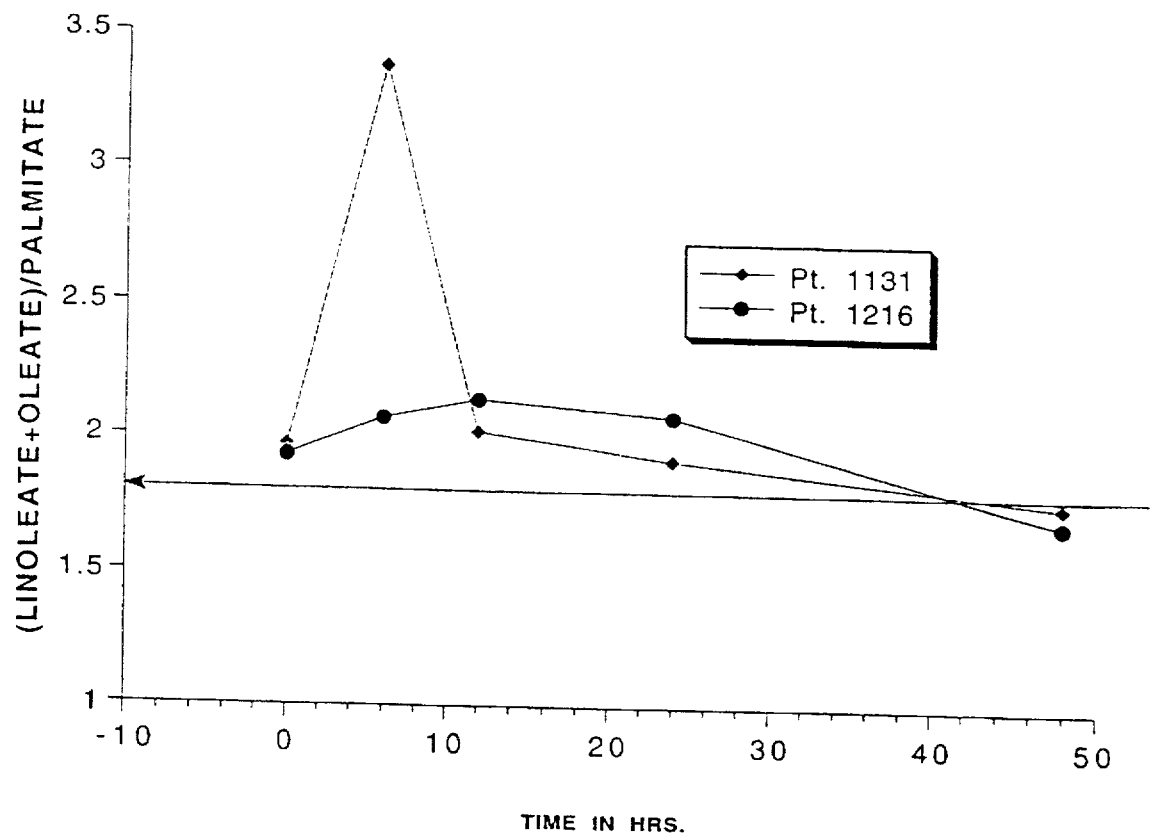
FIG. 7 shows ratio of (linoleate+oleate) divided by palmitate in Group I, septic patients, who developed ARDS, were admitted to the trauma center with higher FFA ratios than controls and the ratios remained high over time.
Figure 8:
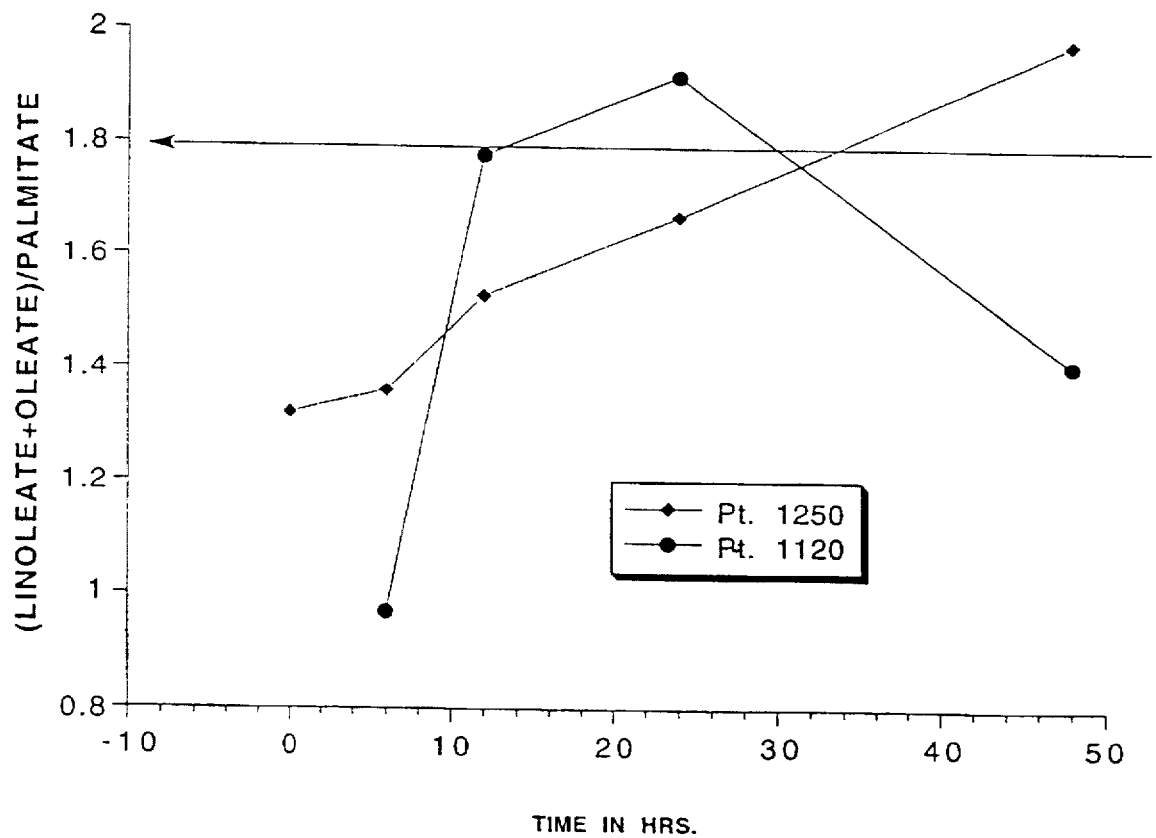
FIG. 8 shows the ratio of (linoleate+oleate) divided by palmitate in Group I, trauma patients, who developed ARDS, were admitted to the trauma center with FFA ratios similar to controls, but the ratios increased with time.
Figure 9:
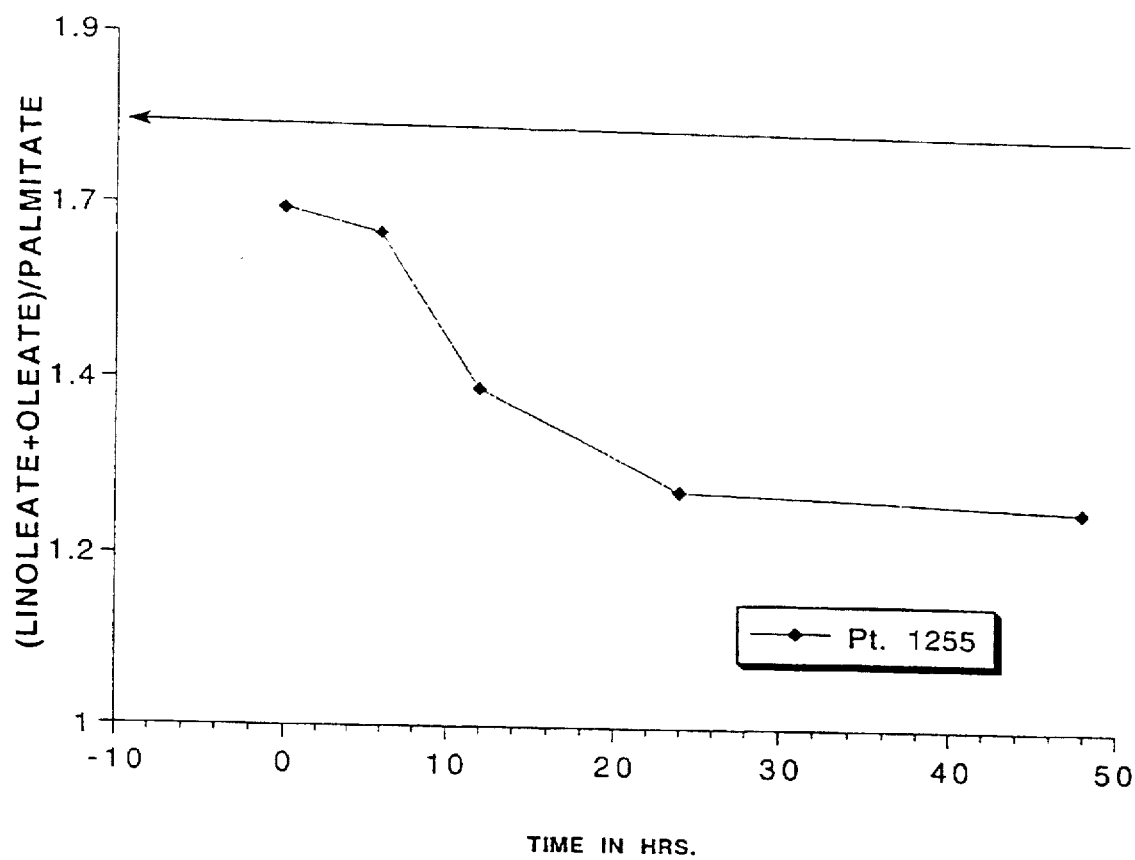
FIG. 9 shows the ratio of (linoleate+oleate) divided by palmitate in a patient that was at risk, but did not develop ARDS.
Figure 10:
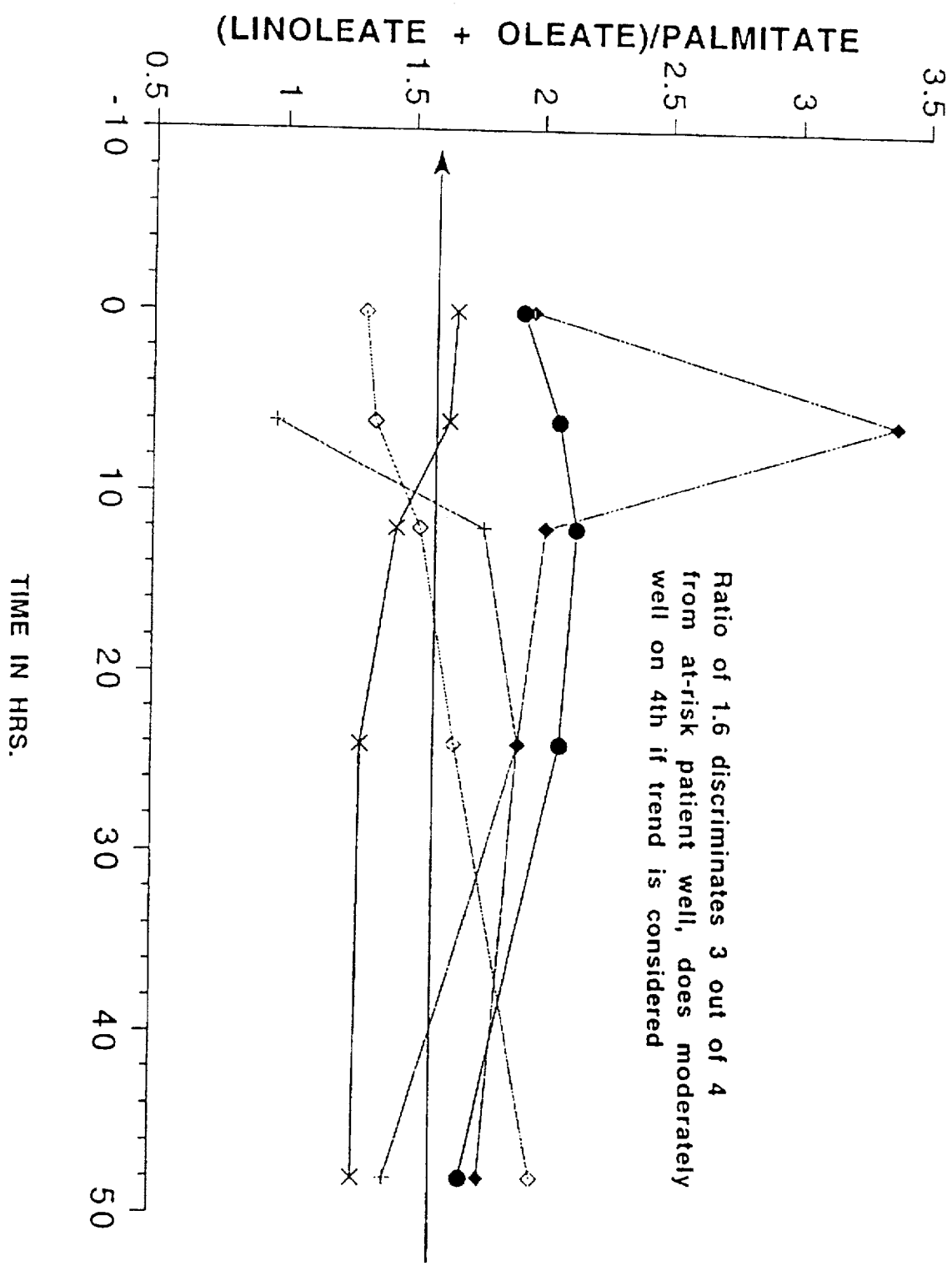
FIG. 10 shows a summary of Group I data. An empirically derived discriminator was drawn at 1.6 to segregate the at risk patients who developed ARDS from those who did not.

The control patients (FIG. 6) were at risk and ill enough to be admitted to the trauma center, but none of them developed ARDS. Group I septic patients with ARDS (FIG. 7) had higher FFA ratios at the time of admission than the controls and the ratios remained high. Group I trauma patients who developed ARDS (FIG. 8) started with FFA ratios similar to the controls, but the ratios increased with time. FIG. 9 shows a patient at risk who did not develop ARDS. The ratio is high initially, but decreases to the control mean level with time. A summary for the Group I samples is shown in FIG. 10. A discriminator line of 1.6 was empirically derived to segregate the patients who developed ARDS from those who did not.

Figure 11:
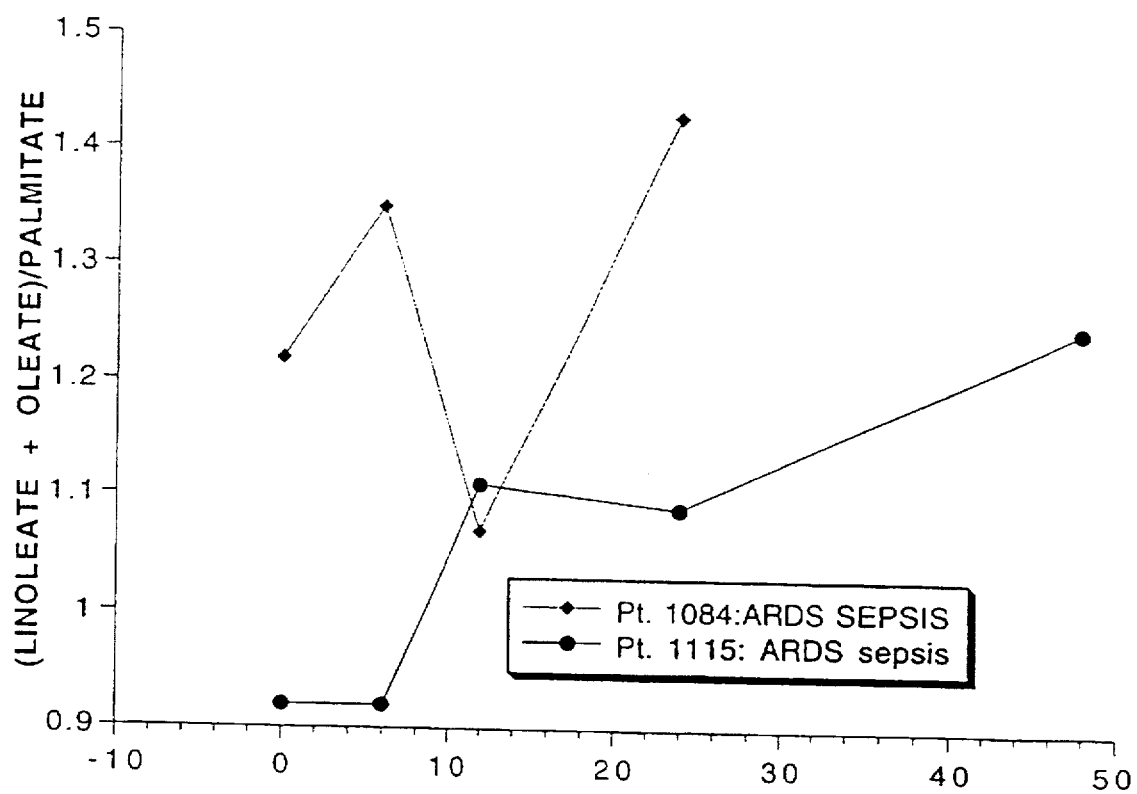
FIG. 11 illustrates the ratio of (linoleate+oleate) divided by palmitate for Group II, septic patients, who developed ARDS, had FFA ratios both lower and higher than control patients, but all ratios increased above the controls with time.
Figure 12:
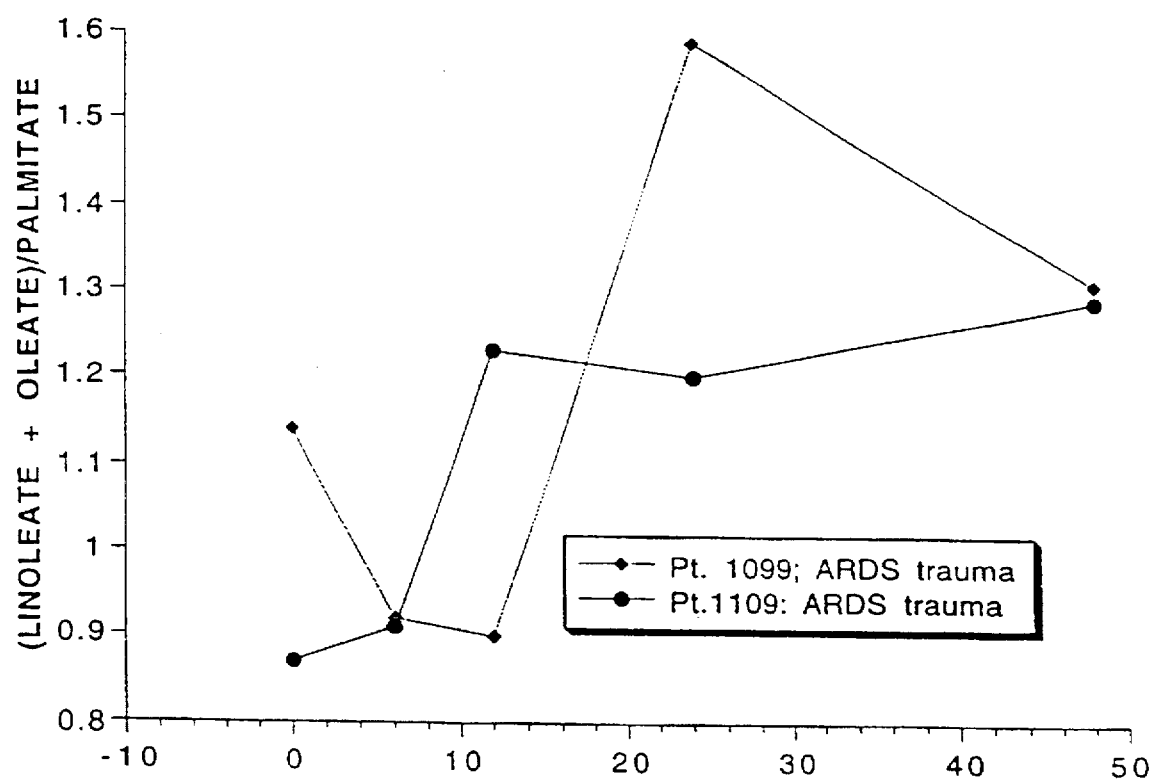
FIG. 12 illustrates the ratio of (linoleate+oleate) divided by palmitate for Group II, trauma patients who developed ARDS. The FFA ratios of both patients rose well above the ratios of the controls with time.
Figure 13:
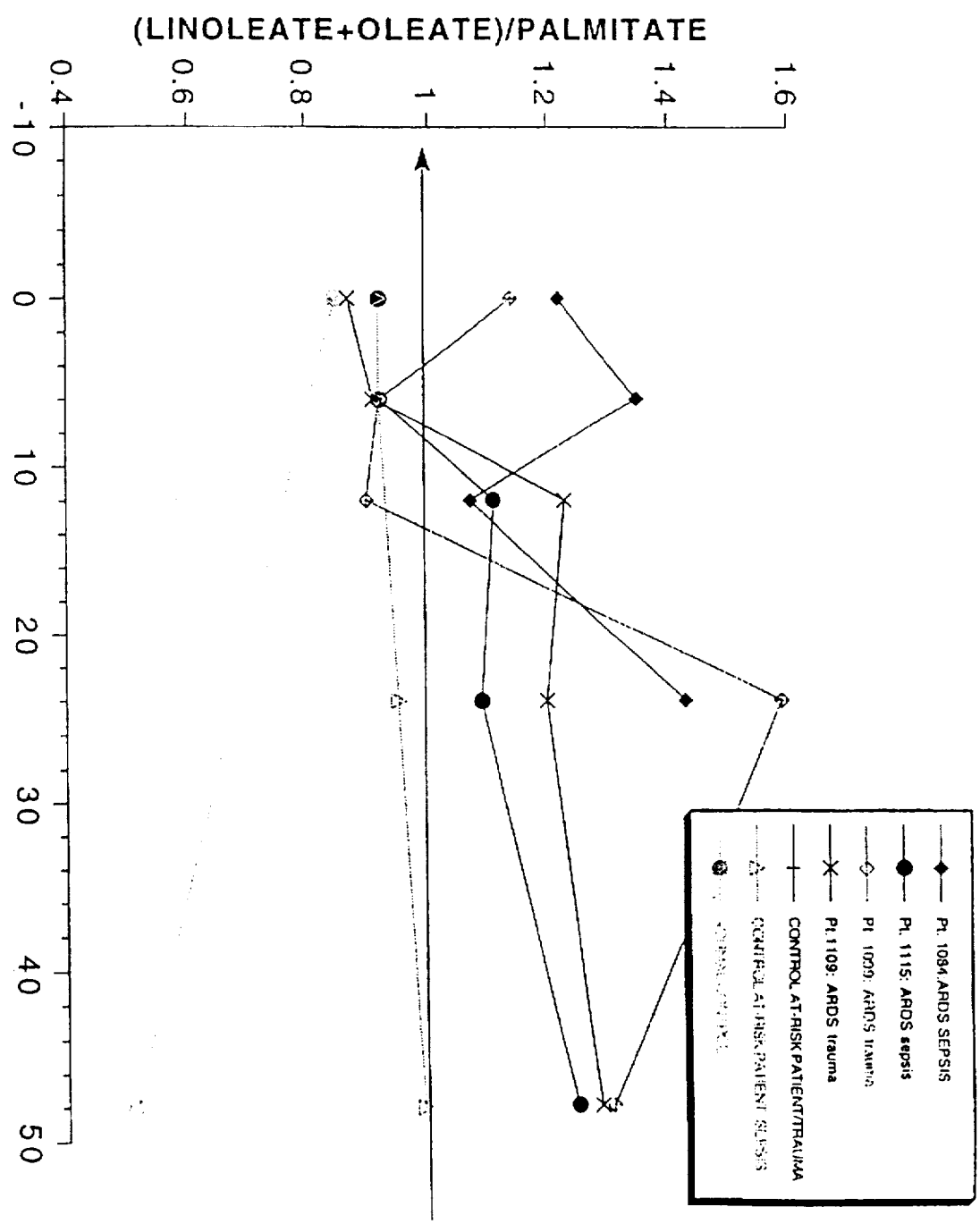
FIG. 13 shows a summary of Group II patients ratios over time. Using a 24 hr discriminator ratio of 1.0 segregates the patients who developed ARDS from those who did not.

In Group II septic patients, FFA ratios either start higher than controls or increased with time (FIG. 11). Trauma patients' ratios either started at control levels or dropped initially, but rose above controls with time (FIG. 12). A summary of the Group II results is presented in FIG. 13. An empirically derived discriminator is drawn at 1.0 to segregate the ARDS patients from the patient controls.

Figure 14:
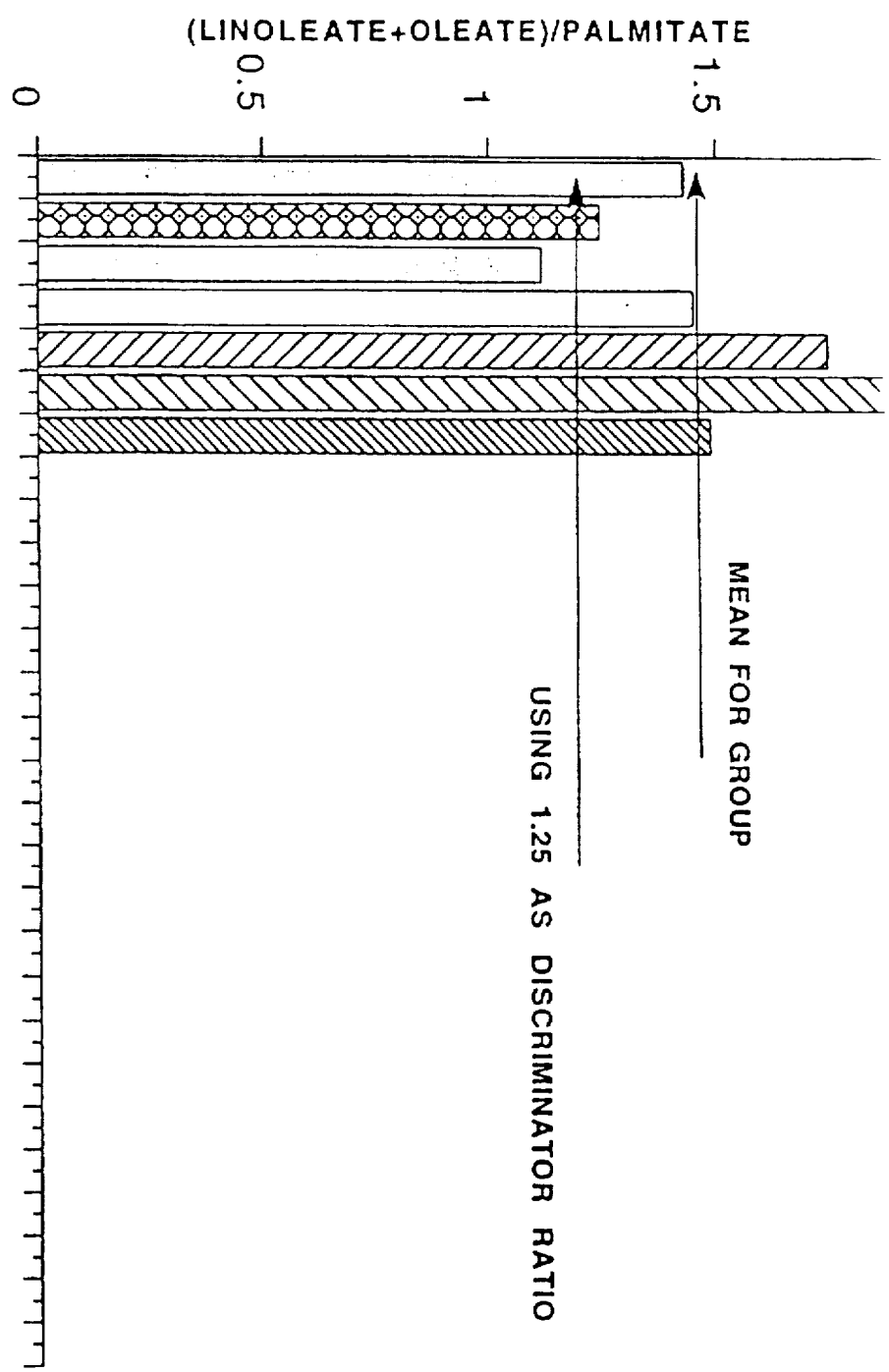
FIG. 14 shows the ratio values for the septic patients who developed ARDS at the 24 hr sample time.
Figure 15:
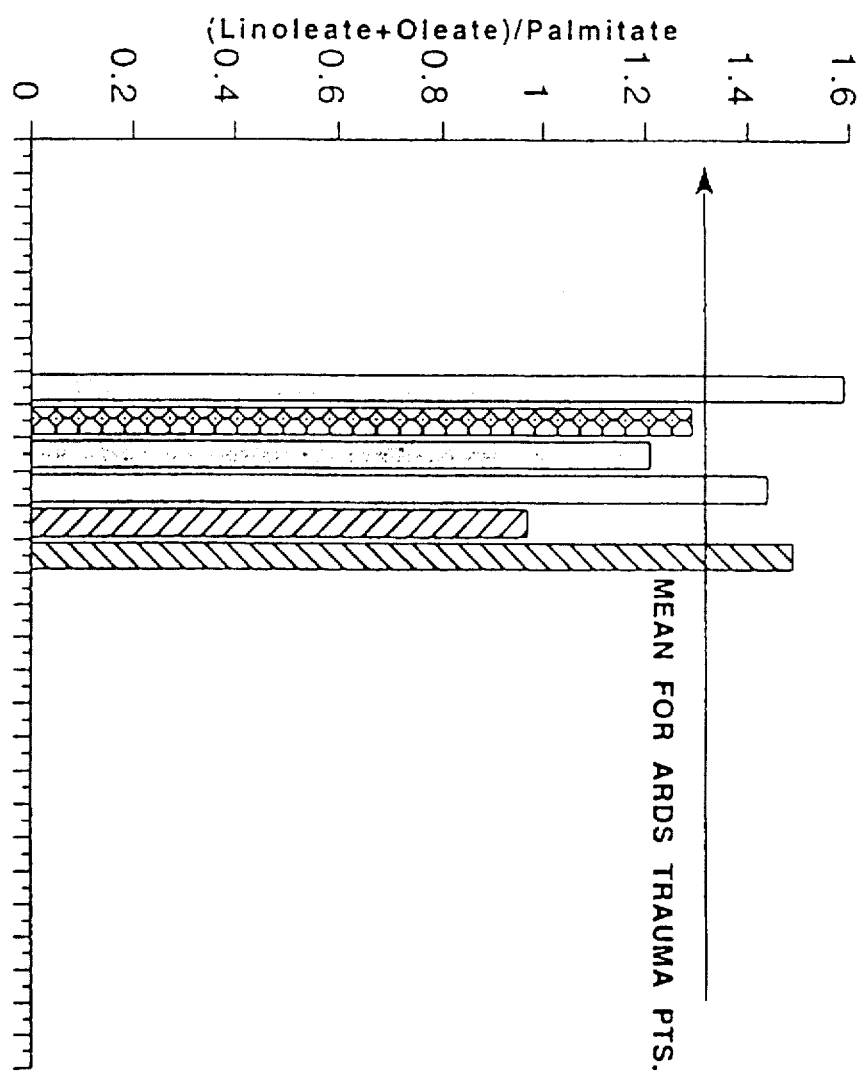
FIG. 15 shows the ratio values for the trauma patients who developed ARDS at the 24 hr sample time.
Figure 16:
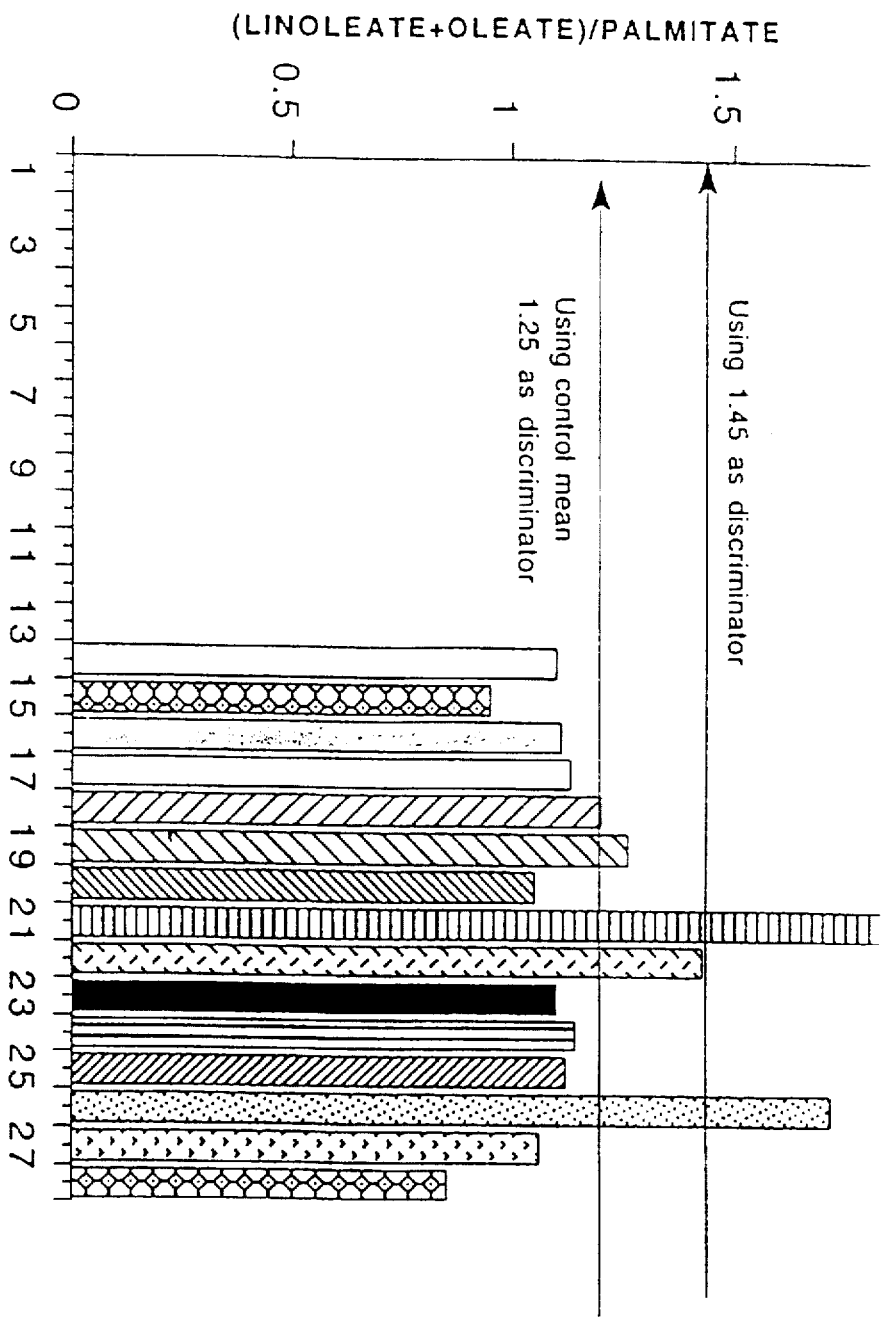
FIG. 16 shows the ratio values for the at risk control patients who did not develop ARDS at the 24 hr sample time.
Figure 17:
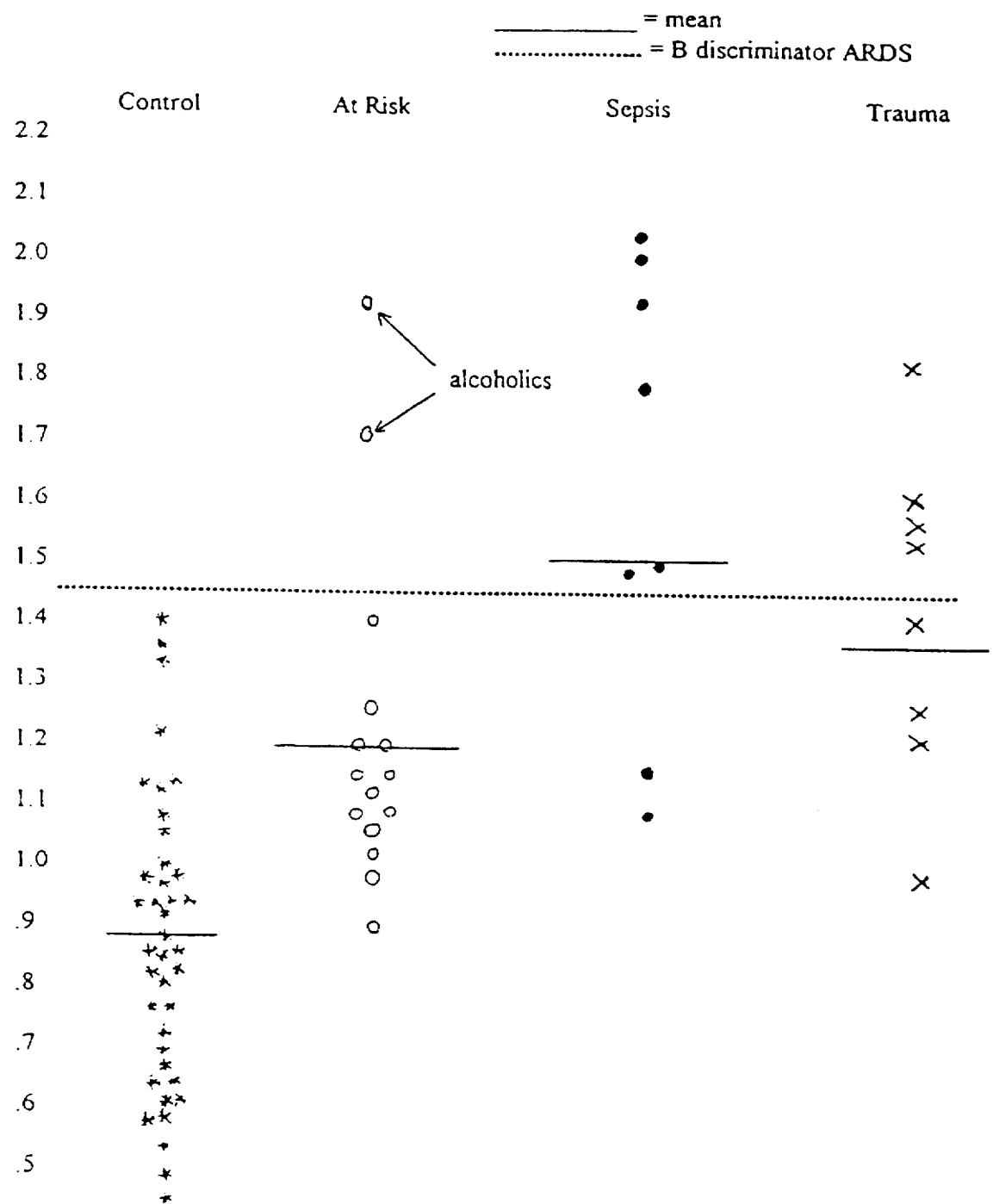
FIG. 17 shows a Bayesian plot of the ratio at 24 hr sample time for control, at risk, sepsis and trauma patients, including two alcoholic patient outliers.

The serum FFA ratios of the single 24 hr samples from Group II. are shown in FIGS. 14 through 16. FIG. 14 shows the ratios for septic patients who developed ARDS. FIG. 15 shows the ratios for trauma patients who developed ARDS. FIG. 16 shows the ratios for the 24 hr control (at risk) patients. A Bayesian plot of all 24 hr data and the normal CTI individuals is shown in FIG. 17. The ratios of the at risk patients are higher than the CTI normal individuals and lower than the ARDS patients. After the sample identification code was broken and the results were matched with the patients records. it was discovered that the two patients who did not develop ARDS with ratios above 1.5 were chronic alcoholics with probable liver damage. As the liver is an important organ in maintaining circulatory FFA levels, the chronic alcoholics' data should probably be treated as outliers with the caveat that alcoholism could effect the prediction model. FIG. 18 is the Bayesian analysis after empirically choosing 1.45 as the discriminator value and using the "at risk" patients as controls. From the analysis it can be seen that the method is a good predictor of ARDS and MOD in general. and an excellent predictor of ARDS and MOD from sepsis.

EXAMPLE 5

Figure 19:
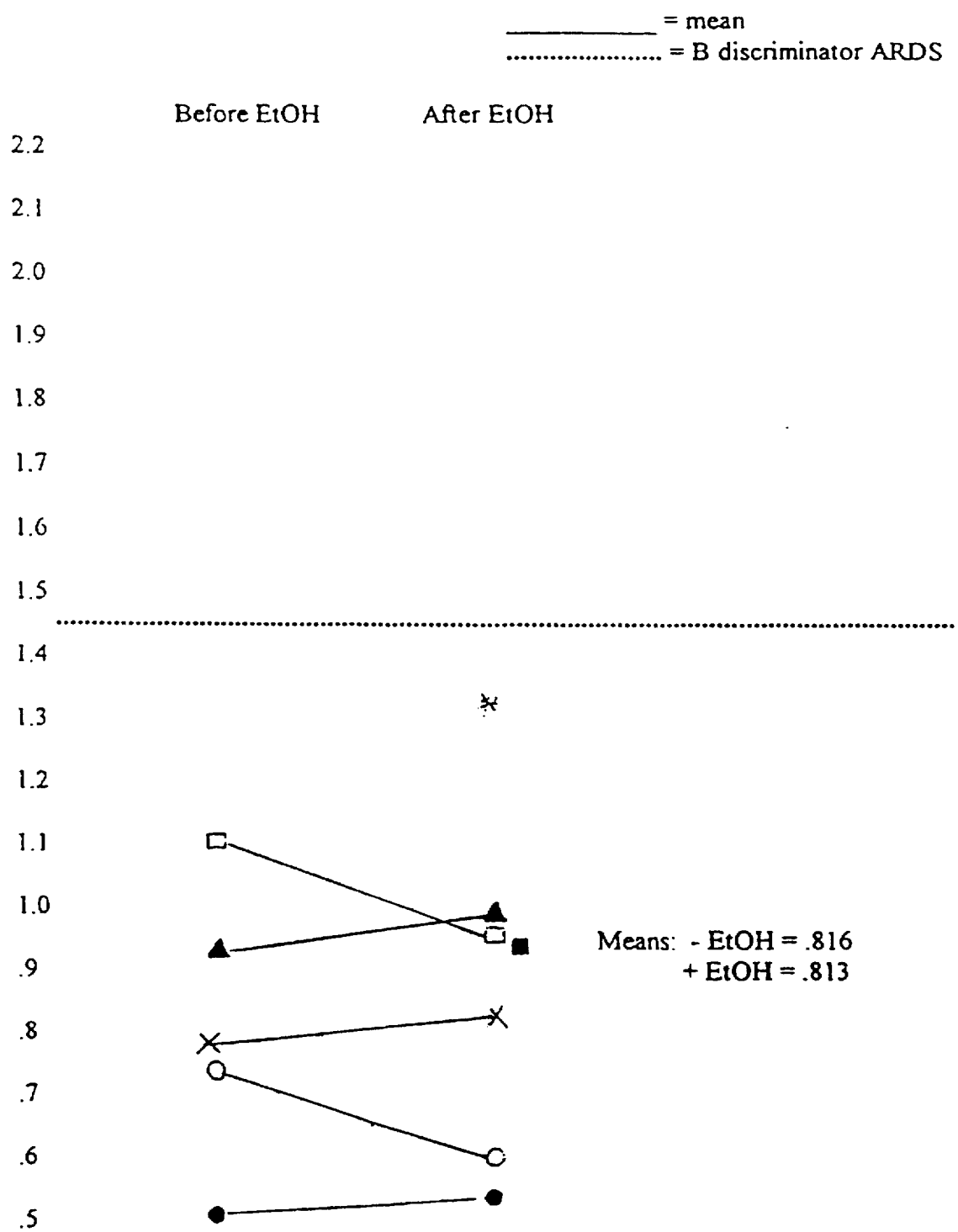
FIG. 19 shows a Bayesian plot of the ratio at 24 hr sample time for control individuals before and after alcohol consumption at a micro brewery.

This example illustrates a small study to determine the effect of alcohol or caffeine consumption on diagnostic test results because of the alcoholics' results reported in example 4. A study to determine if casual alcohol use would affect the FFA results was run. A group of normal control individuals (CTI employees. Seattle Wash.) were tested before and 14 hours after the consumption of several ounces of ethanol (beer from Seattle Wash. micro brewery). FIG. 19 shows no significant overall difference in FFA ratios. The mean values remain virtually the same. Therefore. alcohol consumption did not affect test results.

Figure 20:
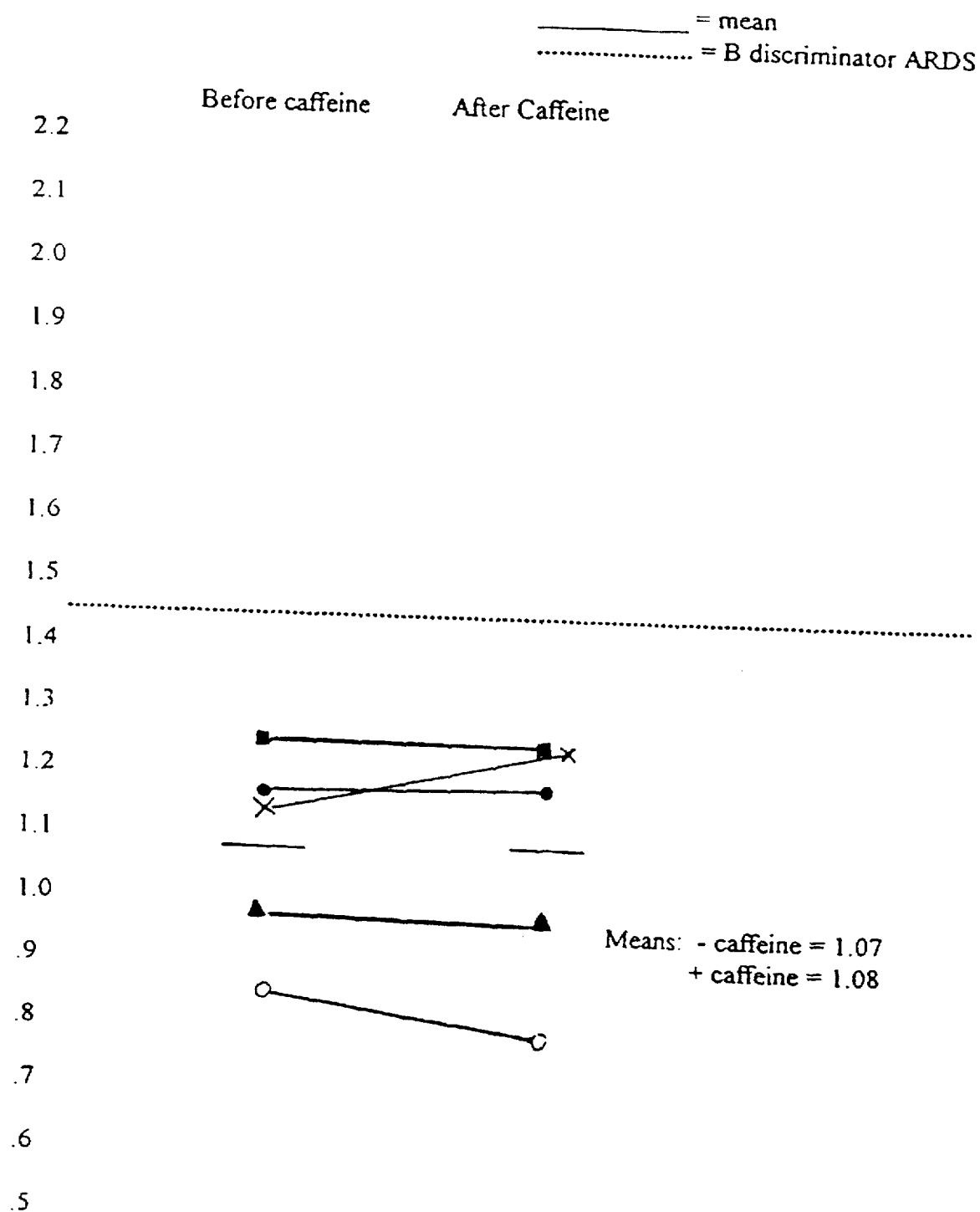
FIG. 20 shows a Bayesian plot of the ratio at 24 hr sample time for control individuals before and after caffeine beverage consumption.

While analyzing the normal control group. it was discovered that most had significant caffeine levels. To determine if caffeine affects the FFA Ratio. a group of normal controls were tested before and after caffeine (unrestricted coffee (Starbucks) consumption). FIG. 20 shows no significant overall difference in FFA ratios. The mean values remain virtually the same. Therefore. caffinated beverage consumption did not affect test results.

We claim:

1. A diagnostic assay for adult respiratory distress syndrome (ARDS). sepsis. multiple organ dysfunction (MOD) and systemic inflammatory response syndrome (SIRS). comprising (a) measuring an amount of unsaturated free fatty acid (FFA) selected from the group consisting of linoleate. oleate. and aracidonate and an amount of saturated free fatty acid (FFA) selected from the group consisting of myristate. palmitate. and stearate in a body fluid. and (b) determining an increased ratio value comprising the amount of selected unsaturated FFA divided by the amount of the selected saturated FFA as compared to a normal value. is diagnostic ARDS. MOD and SIRS.

2. A diagnostic assay of claim 1. wherein the unsaturated FFA is linoleate and oleate and the saturated FFA is palmitate.

3. The diagnostic assay of claim 1 wherein the body fluid is plasma. urine. sweat. saliva or tears.

4. The diagnostic assay of claim 1 wherein measuring is conducted using at least one of a technique selected from the group consisting of HPLC (high performance liquid chromatography). GC (gas chromatography). TLC (thin layer chromatography) and immunoassays using antibodies specific for a particular FFA.

5. The diagnostic assay of claim 2. wherein the body fluid is plasma.

6. The diagnostic assay of claim 3. wherein the body fluid is plasma.

\* \* \* \* \*